United States Patent

Hessel et al.

Patent Number: 5,098,427
Date of Patent: Mar. 24, 1992

[54] SURGICAL LASER INSTRUMENT

[75] Inventors: Stefan Hessel; Gerhard Hauptmann, both of Munich, Fed. Rep. of Germany

[73] Assignee: Messerschmitt-Bölkow-Blohm GmbH, Fed. Rep. of Germany

[21] Appl. No.: 597,799

[22] Filed: Oct. 10, 1990

[30] Foreign Application Priority Data

Oct. 17, 1989 [DE] Fed. Rep. of Germany ....... 3934647

[51] Int. Cl.$^5$ .............................................. A61B 17/36
[52] U.S. Cl. ........................................ 606/11; 606/15; 606/16; 128/398; 219/121.62
[58] Field of Search .................. 606/2, 3, 7, 8, 10–19; 128/395–398; 219/121.6–121.62

[56] References Cited

U.S. PATENT DOCUMENTS

| | | | |
|---|---|---|---|
| 4,519,390 | 5/1985 | Horne | 606/15 |
| 4,693,244 | 9/1987 | Daikuzono | 606/16 |
| 4,702,245 | 10/1987 | Schröder et al. | |
| 4,719,912 | 1/1988 | Weinberg | 606/4 |
| 4,741,612 | 5/1988 | Birngruber et al. | 351/221 |
| 4,938,205 | 7/1990 | Nudelman | 128/6 |
| 4,939,336 | 7/1990 | Meyer et al. | 219/121.62 |

FOREIGN PATENT DOCUMENTS 0292622 5/1987 European Pat. Off.
3813918 1/1988 Fed. Rep. of Germany.

OTHER PUBLICATIONS

Brochure (2 pages) Medical Excimer Laser, Technolas Laser Technick GmbH, Lochhamer Schlag 19, D-8032 Gräfelfing, W. Germany, May 17, 1990.

Primary Examiner—Stephen C. Pellegrino
Assistant Examiner—Steven J. Shumaker
Attorney, Agent, or Firm—Evenson, Wands, Edwards, Lenahan & McKeown

[57] ABSTRACT

A surgical laser instrument suitable for the alternate contant cutting and no-contact coagulating of biological tissue by means of a fiber-optically guided irradiation of a laser. Radiation which is emitted by the pyrolytic glowing of at least partially carbonized biological tissue, is received by the distal end of the fiber-optic light guide, guided back to a radiation detector, and is detected in a spectral region between 0.3 and 0.9 μm, while the laser radiation is filtered out. The radiation output of the laser is controlled by means of the detector output signal, to a value under the destruction threshold of the fiber-optic light guide in such a manner that the radiation emitted during the burning of the biological tissue to be cut as well as of the tissue residues adhering to the distal end of the fiber-optic light guide and burnt into it, does not exceed a predetermined value.

5 Claims, 3 Drawing Sheets

SURGICAL LASER INSTRUMENT

BACKGROUND AND SUMMARY OF THE INVENTION

The invention relates to a surgical laser instrument for the alternate contact cutting and no-contact coagulating of biological tissue by means of a fiber-optically guided irradiation of a laser which, for this purpose, is connected with a fiber-optic light guide as the cutting and coagulation instrument.

In laser surgery, contact cutting is frequently preferred over no-contact cutting because it is difficult to guide the fiber-optic instrument at a uniform distance above the tissue. In addition, in the case of the previous laser systems, it is essential that the optical fiber not be brought in contact with the tissue during the irradiation because the tissue residues adhering to the fiber immediately burn into the fiber and ultimately lead to an overheating and breakage of the fiber. For this reason, a surgical laser instrument is suggested in the U.S. Pat. No. 4,693,244 which, for the purpose of contact cutting, carries a sapphire tip at the end of an optical fiber which better withstands thermal stress during contact cutting. These sapphire tips which have already been introduced into laser surgery, however, are relatively expensive and expediently are suitable only for cutting. In addition, the service life of sapphire tips of this type is limited and is drastically reduced in the case of improper handling. Finally, it is difficult to achieve a targeted coagulation under constant visual control of the respective irradiated patch of tissue.

It is therefore an object of the invention to provide a surgical laser instrument for the alternate contact cutting and no-contact coagulating of biological tissue by means of a fiber-optically guided irradiation of a laser which provides high technical safety requirements, particularly with respect to the service life of the fiber-optic light guide, and at the same time permits more diverse work than by means of the known instrument.

This object is achieved by means of a surgical laser instrument according to the invention in which the light emitted in the visible spectral region between 0.3 and 0.9 $\mu$m ("white light"), due to pyrolytic glowing of biological tissue which has been at least partially carbonized due to the impinging laser radiation, is detected and is used for controlling the output of the laser. In this case, the term "fiber-optic light guide" applies to all components which guide the laser light to the tissue to be treated, so that this protection applies to the use of the naked fiber as a cutting and coagulation instrument as well as to those fiber-optic light guides in which an applicator is made of an at least partially optically transparent material, such as a sapphire tip, coupled to the distal end of the optical fiber.

An arrangement for the laser treatment of tissue is disclosed in German Patent document DE 38 13 918 A1, in which a sensor detects the fluorescent radiation originating from the treated tissue as a result of the impinging laser radiation, and permits an identification of the tissue by means of a spectral analysis unit. Because of this information, the laser irradiation may be optimized. However, the objects of the present invention cannot be achieved in this manner, particularly since the fluorescent radiation emitted by the tissue does not furnish any clear information with respect to the thermal stressing of the light guide. By contrast, the Laser surgical instrument according to the invention detects the carbonization of the biological tissue (and hence, the direct thermal stressing of the fiber during the carbonization of the tissue residues adhering to the distal end of the fiber), and by controlling the laser output, ensures that the destruction threshold of the light guide material is not exceeded. Uniform contact cutting in the tissue is thus achieved.

If, after the contact cutting, certain tissue parts are to be coagulated in a no-contact manner, it is sufficient to pull the light guide contaminated by tissue residue out of the incision and to hold it in front of the tissue area to be coagulated at a distance that can be observed well. Since the radiation that previously had been emitted mainly by the tissue to be cut is now absent, the radiation output of the laser is increased until the tissue residues on the light guide re completely carbonized and burned up. The resulting irradiation therefore reaches a predetermined value which represents the destruction threshold of the light guide. The fiber end will then become increasingly more transparent for the laser radiation so that the laser is controlled upward to a predetermined output limit, and may then be used for the coagulating with a sufficient distance between the fiber end and the tissue. Surprisingly, the invention therefore solves several problems so that, in contrast to prior art devices, an alternate contact cutting as well as a no-contact coagulating becomes possible even by means of the bare fiber while the service life is prolonged.

Other objects, advantages and novel features of the present invention will become apparent from the following detailed description of the invention when considered in conjunction with the accompanying drawings.

BRIEF DESCRIPTION OF THE DRAWINGS

The invention will be described in the following by means of the embodiments shown partially schematically in the figures.

DETAILED DESCRIPTION OF THE DRAWINGS

Figure 1:
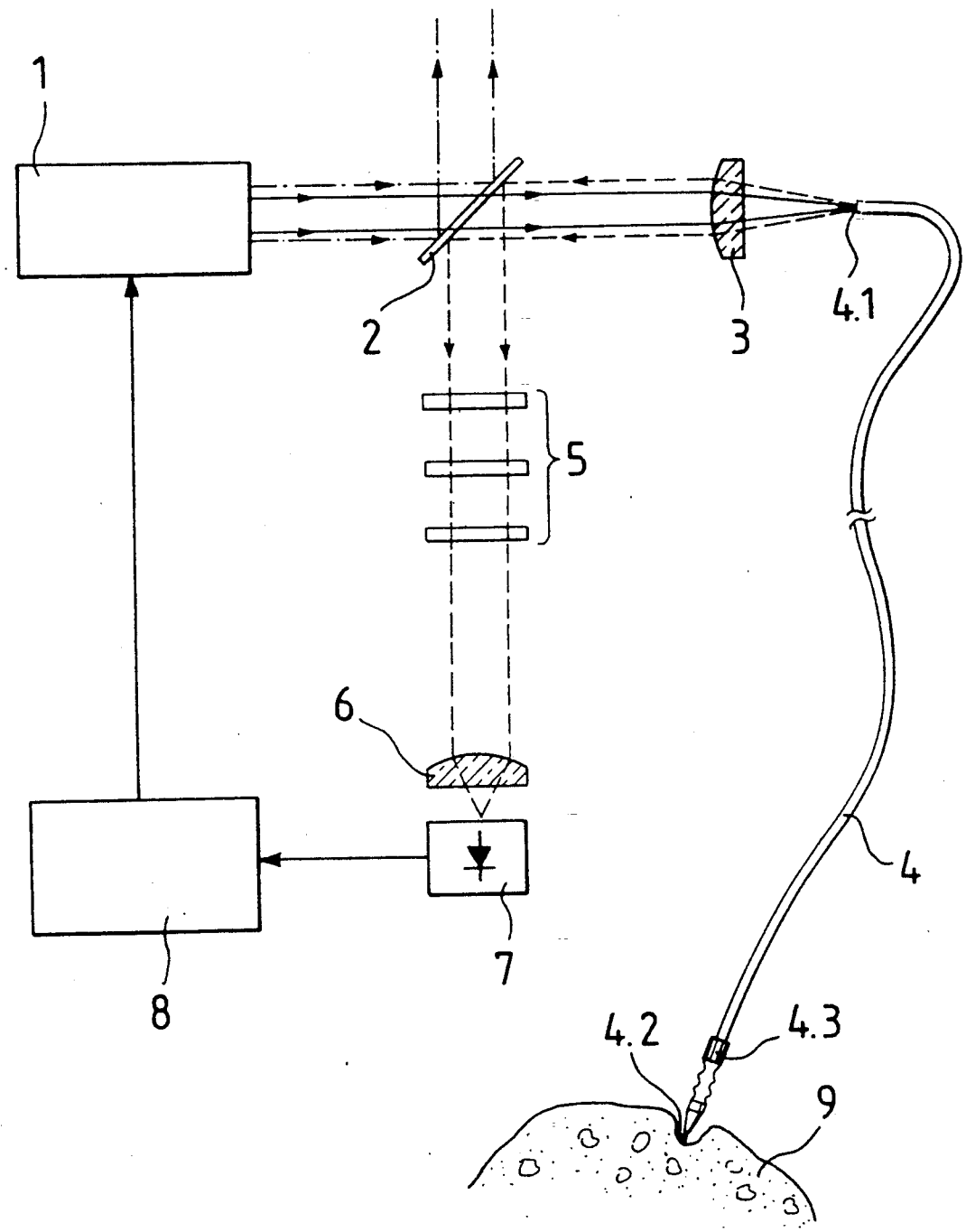
FIG. 1 is a view of a surgical laser instrument for free-hand work.

In the embodiment illustrated in FIG. 1, the radiation of a medical laser 1 is coupled into the proximal end 4.1 of an optical fiber 4 by way of a wavelength-selective beam splitter 2 and a lens system 3. The laser instrument 1 is a Neodym YAG therapy laser with radiation that is at approximately 1 $\mu$m, that is, in the short infrared range. Beam splitter 2 is constructed as a wavelength-selective mirror, with the coatings selected such that the radiation of the Neodym YAG laser can pass through unimpaired, while the radiation emitted by the pump light sources on the laser side 20 (mainly in the visible range), as well as the radiation returned on the light guide side 22, are reflected in the spectral region between 0.3 and 0.9 $\mu$m. The radiation 21 reflected on the laser side 20 is diverted or absorbed in an unutilized manner, while the radiation 23 reflected on the light guide side, by way of a filter system 5 and another lens system 6, reaches a radiation detector 7, the output signal of which is analyzed in an electronic control circuit 8, and is used for controlling the laser 1. The latter may take place, for example, by regulating the power supply for the pump light source.

The therapy radiation coupled into the optical fiber 4 is aimed at the tissue 9 to be treated, for the purpose of which the distal end 4.2 of the light guide is surrounded by a handpiece 4.3. The distal end 4.2 of the optical fiber projects a few millimeters out of this handpiece 4.3 and is freed of its cladding (buffer) in the area of the most extreme tip.

Figure 3:
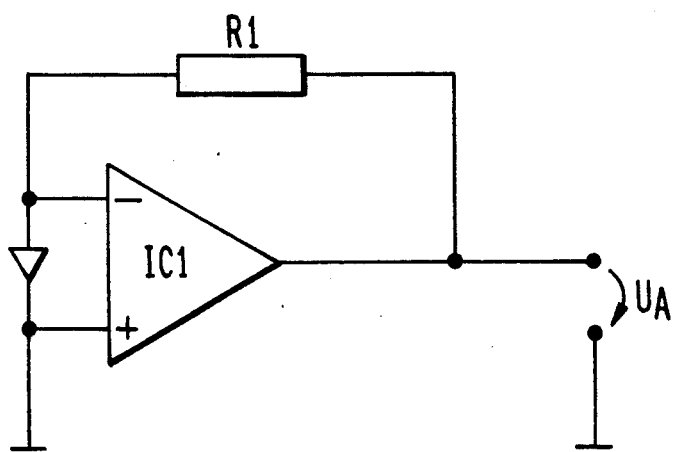
FIG. 3 shows a radiation detector of the type indicated in FIGS. 1 and 2.

As illustrated in FIG. 3, radiation detector 3 is comprised of a photodiode D1 (such as for example, Siemens PBX 60 model) and a power voltage converter IC1 (such as National Semiconductor mode LF356). Light impinging on diode D1 is converted to a voltage signal $U_A$ proportional to the light intensity, with the amplification being adjusted by the resistor R1. Electronic control unit 8, on the other hand, may consist of a microcomputer assembly system such as Siemens model AMS-M6-A8, which controls laser 1 by regulating its power supply in a conventional manner.

Referring again to FIG. 1, the radiation emitted during carbonization of the irradiated tissue, which includes the essential range of the visible spectrum, is received by the distal end 4.2 of the optical fiber, and is guided back by way of this optical fiber and impinges on the beam splitter 2. At the layer of the beam splitter 2 that has the wavelength-selective effect, the radiation 23 is deflected out of the beam path of the laser 1 in the direction of the radiation detector 7. In order to limit the received radiation to the so-called white-light region, the optical filter 5 is designed as a band-pass filter for the region between 0.3 and 0.9 $\mu$m, preferably between 0.4 and 0.8 $\mu$m. For the spectral regions to be filtered out, the damping of the filter should be better than $10^5$.

In response to the signal received from radiation detector 7, electronic control unit 8 controls the output of laser 1 so as to prevent the received radiation output in the detector 7 from exceeding a predetermined value which corresponds to the destruction threshold of the light guide which is used.

Figure 2:
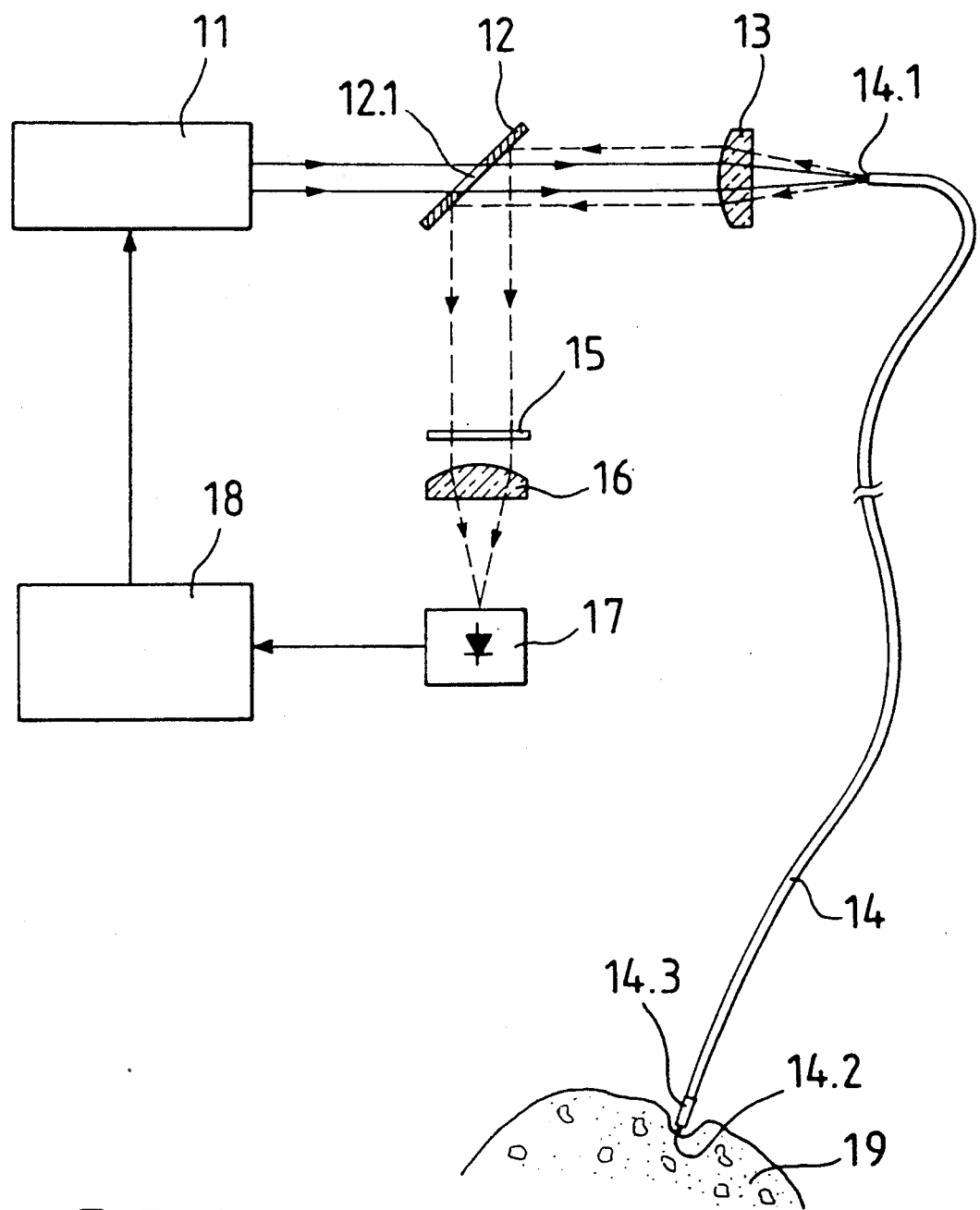
FIG. 2 is a view of a surgical laser instrument for endoscopic purposes.

The embodiment according to FIG. 2 differs from the preceding embodiment mainly because of the fact that it is used for endoscopic purposes. For this purpose, the distal end of the optical fiber 14 has a cladding 14.3 that is visible in x-ray light. The beam splitter 12 between the laser 11 and the coupling-in lens system 13 in this case consists of a wide-band reflector, such as a metallic mirror, with an opening 12.1 in the center, through which the therapy radiation of the laser 11 can pass unimpaired. Thereafter, the radiation is coupled into the optical fiber 14 by way of the lens system 13. The light in the spectral region between 0.3 and 0.9 $\mu$m emitted by the pyrolytic glowing of at least partially carbonized biological tissue 19 is received in turn by the distal end 14.2 of the optical fiber 14, is guided back and, at the proximal end 14.1, is radiated with the full aperture angle of the fiber. The cross-section of the returned radiation beam 24 which is generated by the lens system 13 is larger than that of the laser radiation, and therefore impinges on the beam splitter 12 outside the opening 12.1. The guided-back radiation is thus reflected at the beam splitter 12 and, by way of a filter 15, which suppresses the spectral region of the laser radiation and by way of a lens system 16, reaches radiation detector 17 which, analogously to the preceding embodiment, emits a signal to a control device 18 which, in turn, controls the laser 11 with respect to its radiation output.

A very hot temperature-controlled so-called "hot tip" may be produced by the fact that a material, such as carbon, which absorbs laser light is embedded into the core layer of the optical fiber 14 at its distal end 14.2. In the absence of air, it only glows up, and its irradiation is maintained at a constant value by means of the control loop.

Although the invention has been described and illustrated in detail, it is to be clearly understood that the same is by way of illustration and example, and is not to be taken by way of limitation. The spirit and scope of the present invention are to be limited only by the terms of the appended claims.

We claim:

1. A surgical laser instrument for alternate contact cutting and no-contact coagulating of biological tissue by means of cladded fiber-optically guided laser radiation, comprising:

a source of laser radiation optically coupled to a fiber-optic light guide having a proximal end and a distal end and being adapted to conduct radiation between said proximal end and said distal end;

said proximal end of said radiation guide being adapted to receive laser radiation from said source of laser radiation, whereby said laser radiation is conducted by said light guide to the distal end thereof;

said distal end being adapted to direct said laser radiation onto biological tissue to be surgically cut, and to receive radiation emitted by pyrolytic glowing of said tissure, whereby said emitted radiation is conducted by said light guide to the proximal end thereof;

detector means coupled in communication with said proximal end of said light guide, for receiving said emitted radiation and for generating an output signal indicative of intensity of said emitted radiation;

means responsive to said output signal from said detector means, for controlling said source of laser radiation to prevent said emitted radiation from exceeding a level corresponding to a destruction threshold of said light guide.

2. A surgical laser instrument according to claim 1, wherein said emitted radiation is detected by said detector means in a spectral region of between 0.3 an 0.9 $\mu$m.

3. A surgical laser instrument according to claim 1, wherein radiation from said source of laser radiation is coupled into the proximal end of the light guide by a beam divider and a lens system arranged in a beam path between said source of laser radiation and from said proximal end of said light guide, said beam divider having the property that it transmits laser radiation from said laser radiation source and reflects laser radiation from said laser radiation source and reflects emitted radiation from said proximal end of said light guide, and being so oriented that reflected radiation from said proximal end of said light guide impinges on said radiation detector means, and wherein the distal end of the light guide is freed from its cladding.

4. A surgical laser instrument according to claim 3, wherein said emitted radiation from the proximal end of said light guide is transmitted to said radiation detector means through a filter disposed between said beam divider and said radiation detector, said filter having the property that it filters out radiation outside the spectral region between 0.3 and 0.9 $\mu$m, as well as laser radiation, and having a damping that is at least $10^5$.

5. Method of controlling a surgical laser instrument comprising the steps of:
generating a laser beam;
guiding said laser beam via a lightguide which conducts said laser beam from a source thereof to biological tissue;
detecting radiation emitted by pyrolytic glowing of at least partially carbonized biological tissue, and
controlling said laser beam in response to intensity of radiation detected from the pyrolytic glowing of said biological tissue, to prevent intensity of said emitted radiation from exceeding a level corresponding to a destruction threshold of said light guide.

* * * * *